US012728264B2

(12) United States Patent
Chacon Martínez et al.

(10) Patent No.: US 12,728,264 B2
(45) Date of Patent: Sep. 8, 2026

(54) DEVICE FOR STIMULATING HAIR GROWTH

(71) Applicant: Mane Biotech GmbH, Cologne (DE)

(72) Inventors: Carlos Andres Chacon Martínez, Cologne (DE); Samuel Christopher Jack Jellard, Cologne (DE)

(73) Assignee: MANE BIOTECH GmbH, Cologne (DE)

( * ) Notice: Subject to any disclaimer, the term of this patent is extended or adjusted under 35 U.S.C. 154(b) by 466 days.

(21) Appl. No.: 18/021,208

(22) PCT Filed: Aug. 18, 2021

(86) PCT No.: PCT/IB2021/057585
§ 371 (c)(1),
(2) Date: Feb. 14, 2023

(87) PCT Pub. No.: WO2022/038529
PCT Pub. Date: Feb. 24, 2022

(65) Prior Publication Data

US 2023/0310853 A1 Oct. 5, 2023

(30) Foreign Application Priority Data

Aug. 19, 2020 (DE) ........................ 102020121715.3

(51) Int. Cl.
*A61N 1/36* (2006.01)
*A61N 1/04* (2006.01)

(52) U.S. Cl.
CPC ....... *A61N 1/36031* (2017.08); *A61N 1/0484* (2013.01)

(58) Field of Classification Search
CPC .. A61N 1/0484; A61N 1/0464; A61N 1/0492; A61N 1/26; A61N 1/322; A61N 1/328
See application file for complete search history.

(56) References Cited

U.S. PATENT DOCUMENTS

2010/0217369 A1* 8/2010 Gross ........................ A61N 1/32 607/139
2016/0001073 A1* 1/2016 Ingman ................ A61N 1/0476 607/148

(Continued)

FOREIGN PATENT DOCUMENTS

KR 100671943 1/2007
WO WO2001002051 1/2001

OTHER PUBLICATIONS

Written Opinion of the International Searching Authority.
International Search Report dated Dec. 3, 2021.

*Primary Examiner* — Alyssa M Alter

(74) *Attorney, Agent, or Firm* — Ralph E. Jocke; Walker & Jocke

(57) ABSTRACT

An apparatus that is configured to stimulate hair growth (100) includes at least one electrode (101). The electrode includes projections such as pins or spikes which extend through the hair of the user and engage a portion of the surface of a user's skin without penetration of the skin. At least one detector (103) is operative to sense at least one condition corresponding to the amount of hair in an area on the user's skin adjacent to the detector. The at least one electrode and at least one detector are in operative connection with control circuitry (102). The control circuitry is operative responsive at least in part to the at least one sensed condition in the area to determine an electrical stimulation pattern (P1-P6) and to cause the electrode to stimulate the area in accordance with the determined pattern.

24 Claims, 6 Drawing Sheets

(56) References Cited

U.S. PATENT DOCUMENTS

| | | | |
|---|---|---|---|
| 2018/0326208 | A1 | 11/2018 | Ingman et al. |
| 2019/0143138 | A1 | 5/2019 | Segal et al. |

* cited by examiner

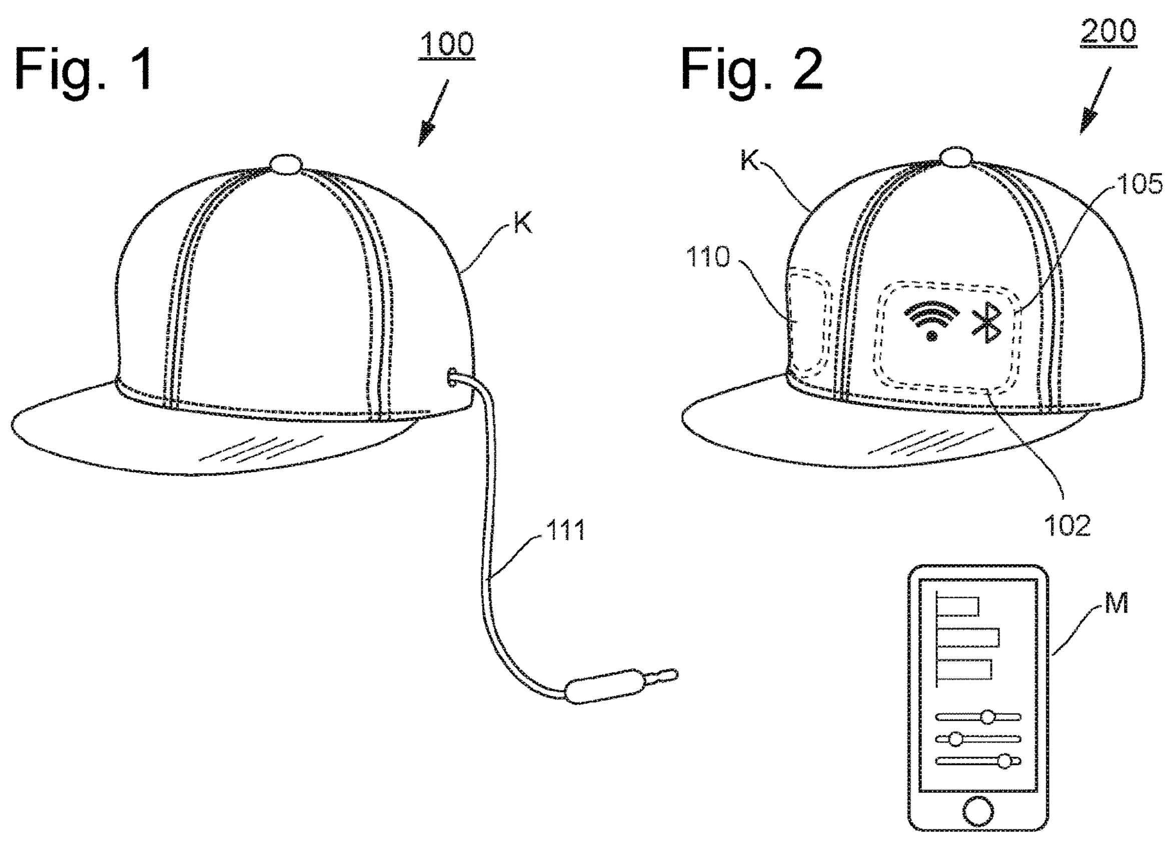
Fig. 1
100
K
111
Fig. 2
200
K
105
110
102
M
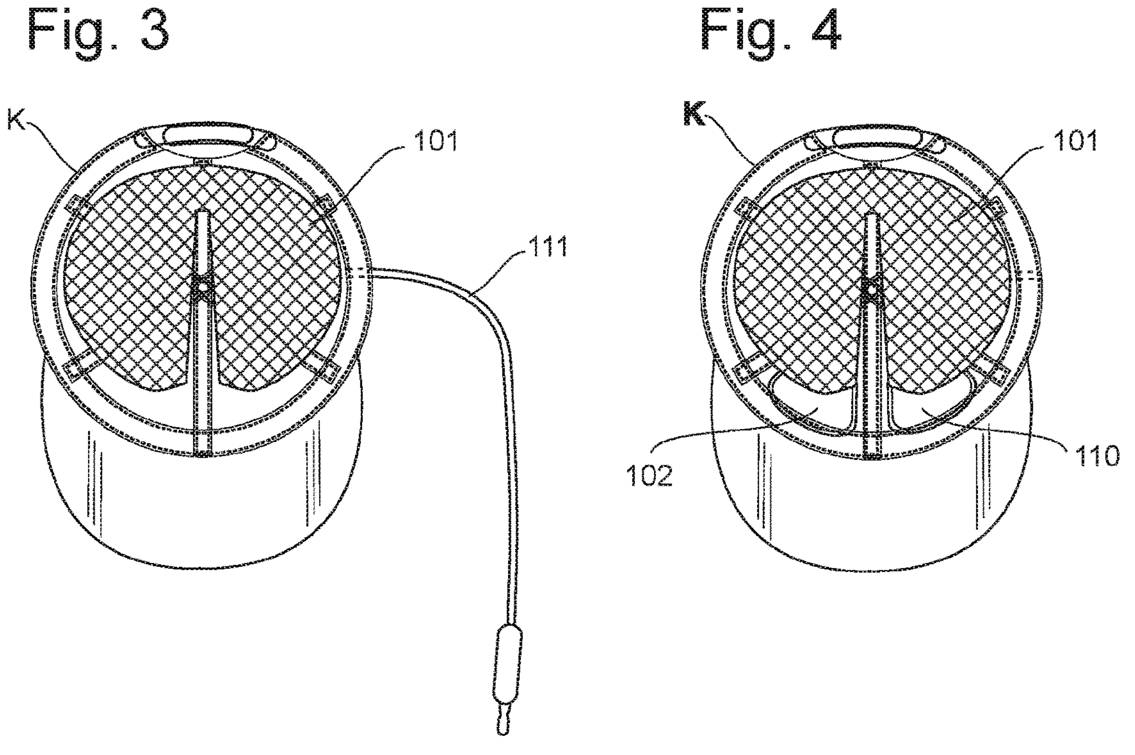
Fig. 3
K
101
111
Fig. 4
K
101
102
110

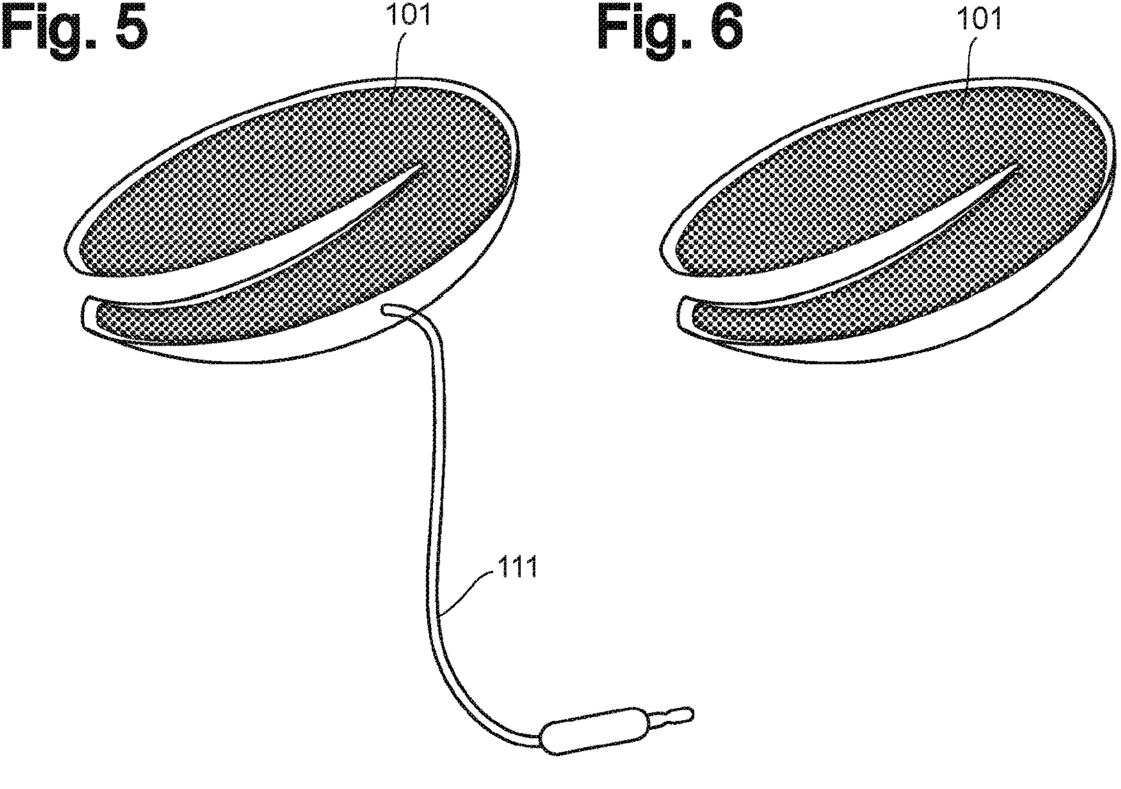
Fig. 5
101
111
Fig. 6
101
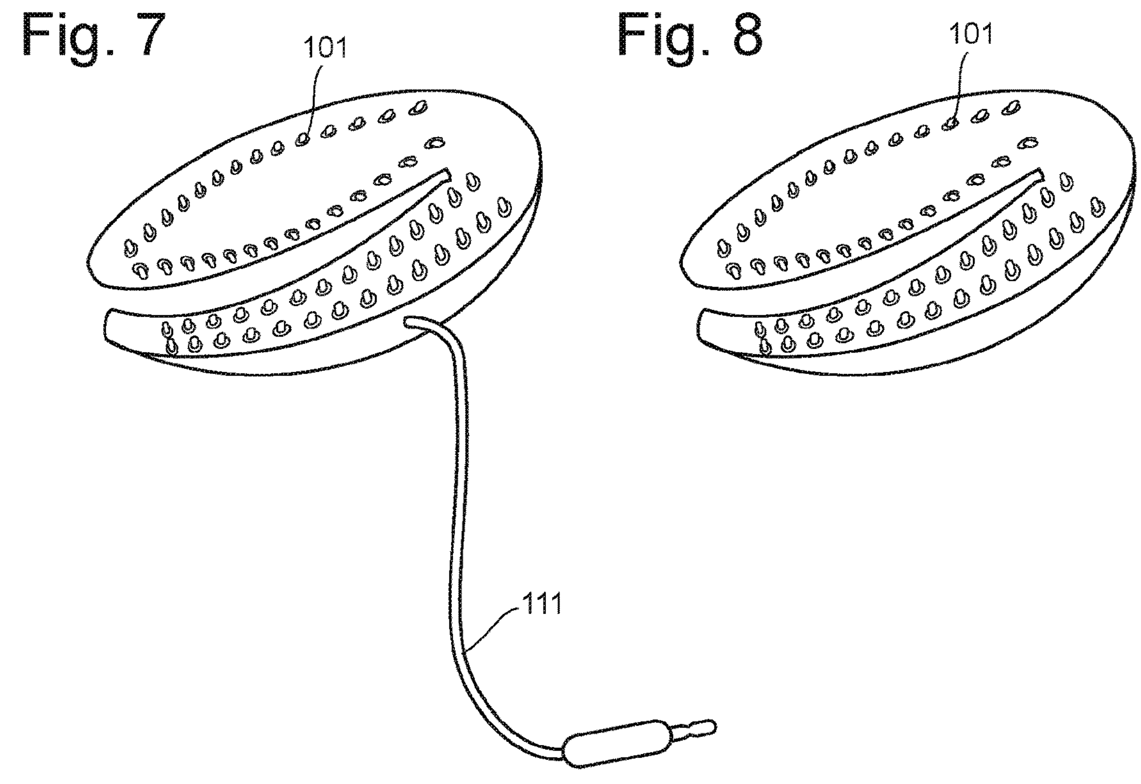
Fig. 7
101
111
Fig. 8
101

Fig. 9A
101
A
A
Fig. 9B
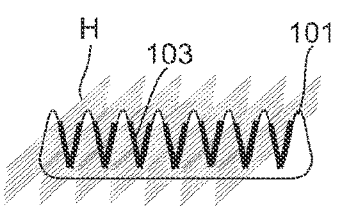
Fig. 10
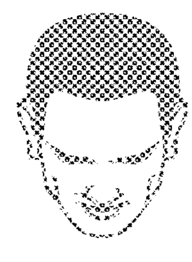
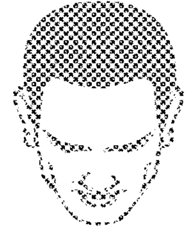
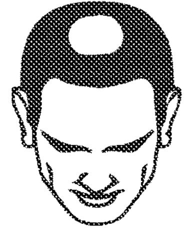
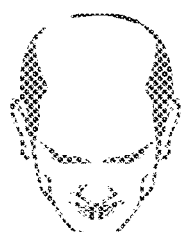
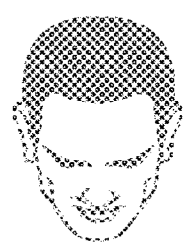
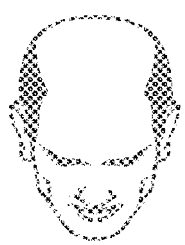
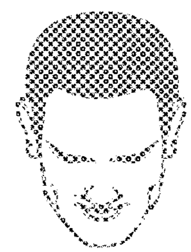
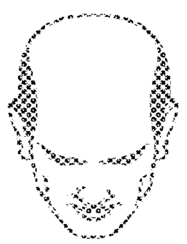

DEVICE FOR STIMULATING HAIR GROWTH

TECHNICAL FIELD

Exemplary arrangements relate to an apparatus for stimulating hair growth. An exemplary arrangement includes at least one electrode for electrically stimulating the skin of a user. A control device connected to the at least one electrode and a detector provides electrical pulses to the at least one electrode in accordance with an electrical stimulation pattern that is determined responsive at least in part to at least one condition sensed by the detector.

BACKGROUND

It is known that electrical stimulation of the scalp at the onset of hair loss can stimulate hair follicles to grow new hair. To stimulate the scalp, it is necessary to place electrodes on the scalp. Electric current flows through the electrodes into the scalp. So far, this method has not been suitable for a therapeutic approach. One reason for this is that the electrical stimulation sometimes has to take place for several hours a day in order to achieve the desired effect.

Korean Patent KR 100 671 943 B1 discloses a hood in which electrodes are present to stimulate hair growth. This hood is worn similar to a bathing cap and is not suitable for daily use by a person who is, for example, in professional life.

US patent publication US 2010/0217369 A1 teaches a helmet-like device in which a control device and electrodes for scalp stimulation are provided.

International patent application WO 01/02051 A1 teaches a magnet arrangement inside a baseball cap to stimulate hair growth.

As previously mentioned, prior devices have the disadvantage that the electrical stimulation must be adapted to the actual hair loss. In the case of circular hair loss, the stimulation should preferably be applied only to the areas of hair loss. Thus, a constant adjustment of the electrodes is necessary. Hair growth stimulation devices in the form of a hood or in the form of a helmet can therefore only be worn in one position. If the stimulation device is worn for a longer period of time, the so-called compliance, i.e. the willingness of the person to wear the device in the predefined position on the head or the ability to wear it because of pressure points, is reduced. It is also possible that with prior devices hair loss is stimulated also and especially in the transition areas from overgrowth to thinned to bald.

To achieve electrical stimulation of the hair follicles, some prior art devices have the electrical impulses introduced into the skin via piercing needle-shaped electrodes. The needles used for this purpose are very thin, like acupuncture needles, and therefore hardly hurt when inserted in the upper layers of the skin. However, piercing electrodes requires a user to overcome a great deal of possible pain after applying them. Needles or electrodes stuck in the skin reduce willingness to use the device even further. The needles stuck in the skin are also stationary. Continuous adjustment of the electrical stimulation is not possible, for example if the device for stimulating the skin is positioned on the head by the user over the course of the day in a similar way to a cap.

Prior art devices may benefit from improvements.

SUMMARY

Exemplary arrangements provide a device for stimulating hair growth with increased comfort and which also automatically adapts the stimulation to the local hair status.

Exemplary arrangements include a control device that is connected to at least one detector. The detectors operate to sense at least one condition that corresponds to the degree of the present hair loss or the degree of hair presence which is alternatively referred to as hairiness. The exemplary control device is operative to determine a preset stimulation pattern for electrical stimulation of the skin responsive at least in part to the at least one sensed condition which corresponds to the detected amount of hair adjacent to the detector.

Thus, exemplary arrangements provide a control and detection device which can measure and detect at least one sensed condition which corresponds to the degree of the actual hair loss status or the degree of hair presence or hairiness. The exemplary control device determines a stimulation pattern depending on the detected hair loss status or hairiness and causes the electrodes to stimulate the skin in accordance with the pattern. The exemplary control and detection device may include temperature sensors, positioning sensors to detect the position of the device on the user's skin or scalp, contact and/or proximity sensors to detect adequate contact of the device with the skin, conductivity sensors to detect change in conductivity of the skin or scalp and adjust at least one parameter of the determined electrical stimulation pattern for providing therapy in accordance with the conditions sensed. For example, if the device detects the loss of hair in the so-called receding hairline, electrodes are preferably applied which provide electrical stimulation pulses in this scalp region. The particular advantage of the constant measurement of the degree of hair loss status or amount of hair on the user's skin in an area adjacent to a detector is that the device adapts to the current position of the stimulation device on the head or on the body part with which it is in contact. It is thus possible to move the device if the wearer and user respond reflexively to a shifting of the device, for example, by a perceived feeling of pressure or by an itching of the scalp or skin at the wearing points.

In some arrangements for reliable detection, foil electrodes can be used which enable sensing an amount of hair on the user's skin in an area of the detector. However, in some arrangements provision is made for the control device to be connected to a plurality of detectors, each individual detector covering and in contact with a predetermined area of the scalp or skin concerned. In this case, the detector can detect the respective degree of local hair loss status or degree of the local hair presence or hairiness via an impedance measurement. Since the hair has an electrically insulating effect on the one hand and also distances an electrode from the skin, the hair acts like a dielectric between the electrically conductive skin and the electrode.

To transmit the electrical stimuli, exemplary arrangements include projections such as pins or spikes on the electrode that have a round tip and protrude through hair that is still present, but rest on the skin or scalp and do not penetrate the skin. The exemplary pins or round spikes comprise projections that are in contact with the skin surface and are non-invasive electrodes.

Moisture and sweat can strongly influence the conductivity of the skin surface. In an exemplary arrangement of the apparatus the control device is furthermore connected to a moisture sensor, which is alternatively referred to herein as a humidity sensor, via which at least one property corresponding the electrical conductivity of the skin can be derived. The exemplary control device operates to change at least one parameter of the present stimulation pattern depending on the detected at least one property by the moisture sensor. In an exemplary arrangement the exemplary control device operates to reduce the level of electrical voltage for stimulating the skin when a sweaty head or sweaty skin is detected, so as not to disturb the user with unpleasant to painful electrical pulses.

In a still further exemplary arrangement of an apparatus for stimulating hair growth the control device is operatively connected to a transceiver for wireless data transmission, such as a BlueTooth® module or a WLAN module. The transceiver may be operated to provide wireless signals indicative of the current status of the control device. It is thus possible in some exemplary arrangements to make the control device intelligent, in which the control device determines a stimulation pattern or program responsive to the user's wearing habits. In some arrangements the intelligence can come from a program in a remote computer, or from a cell phone with sufficient computing power. Furthermore, the transceiver may communicate data to and receive signals from a remote treating physician who controls and monitors the hair growth therapy. It is not only possible that the data from the exemplary hair growth stimulation device is delivered to the outside, but it is also possible that the device behavior can be controlled via control of the control device from the outside, in which data flow is directed to the control device from the outside. It may thus be provided that in some arrangements that the control device is further connected to a transceiver for wireless message transmission, such as a BlueTooth® module or a WLAN module, via which the status and/or operation of the control device is changeable in response to receipt of wireless signals. A change of the status can be that the activated electrodes providing electrical stimulation are adjusted, that the parameters for the recognition of the stimulation-worthy areas are adjusted externally or also that a stimulation pattern or predefined program for stimulation is adjusted.

In exemplary arrangements it can be provided that the apparatus is constructed in the form of a wearable device such as a hat which is also referenced herein as a cap. The at least one electrode and the at least one detector are arranged in operatively supported connection with the hat such as within the area of the hat into which a user's head is received. Thereby, the location of the electrode and the location of the at least one detector device is in a hat lining and in contact with the user's skin.

In some exemplary arrangements it is provided that within the hat there is an accumulator which is alternatively referred to herein as a battery or a power supply. This makes the wearer independent of an external power supply and also of a cable that may lead to a power source worn externally of the hat on the body. In order to charge the accumulator, it may be provided that the hat has a power supply cable for charging the accumulator, or that a coil is provided in the hat for inductively charging the accumulator. The hair growth stimulation device in the form of a hat or in the form of a cap can then be inductively charged on a storage device such as a stand which in some arrangements may be similar to a wig stand, but configured with a coil or other device for charging the accumulator.

To stimulate hair growth, it can be provided that the control device which is alternatively referred to herein as control circuitry, causes the electrical stimulation of the skin within the following electrical parameters: 1 V to 160 V, 1 nC to 1 μC, pulses from 1 Hz to 100 Hz. Thus, short pulses in which an electrical voltage is applied and withdrawn between 1 V and 160 V are directed on to the surface of the skin. Within one pulse, a charge between 1 nC and one μC is discharged on the skin and this with a frequency between 1 Hz and 100 Hz. In exemplary arrangements the electrical stimulation of the skin is carried out in such a way that the user does not receive an electric shock. In an exemplary arrangement when stimulating with 160 V pulses, the charge is so low, for example several nC, that no electric shock is felt by the user despite the high voltage. With lower voltages in the single-digit volt range, the charge can already be considerably greater. In general, either a high voltage or a larger current per area of the user's skin is suitable as an electrical stimulus. In the case of very short time duration electrical pulses, it does not make sense to define from an electric current, because the cross-section on the skin widens considerably and there are different contacts through the electrodes, which can be point contacts but also area contacts. In some arrangements in order to improve the effect of the electrical stimulation, it has been found to be useful if it is provided that the electrical pulses applied responsive to operation of the control device start with an electrical depolarization of the skin with a negative voltage pulse and continue with an immediately subsequent polarization of the skin via a positive voltage pulse. The effect of the electrical pulses on the stimulation of the skin may be enhanced by the brief depolarization followed by polarization.

Further useful aspects of exemplary arrangements are described in the following detailed description.

BRIEF DESCRIPTION OF DRAWINGS

FIG. 1 is a perspective view of a first arrangement of a device for electrical stimulation of the scalp for stimulating hair growth in the form of a hat with an electrical supply cable.

FIG. 2 is a perspective view of a second arrangement of a device for electrical stimulation of the scalp in the form of a hat with an accumulator and a device for wireless data transmission.

FIG. 3 is a bottom view of the device from FIG. 1 with a view of the hat chuck.

FIG. 4 is a bottom view of the device from FIG. 2 with a view of the hat chuck.

FIG. 5 is a perspective view of a stimulation electrode of the device shown in FIG. 1.

FIG. 6 is a perspective view of a stimulation electrode of the device shown in FIG. 2.

FIG. 7 is a perspective view of an alternative stimulation electrode with contact tips for the device according to FIG. 1.

FIG. 8 is a perspective view of a further alternative stimulation electrode with contact tips for the device according to FIG. 2.

FIG. 9A is a perspective view of yet another alternative stimulation electrode with contact tips for the device according to FIG. 1 or FIG. 2.

FIG. 9B is a transverse cross section of the stimulation electrode of FIG. 9A taken along line A-A.

FIG. 10 includes illustrations of typical stages of hair loss in a male.

DETAILED DESCRIPTION

Figure 11:
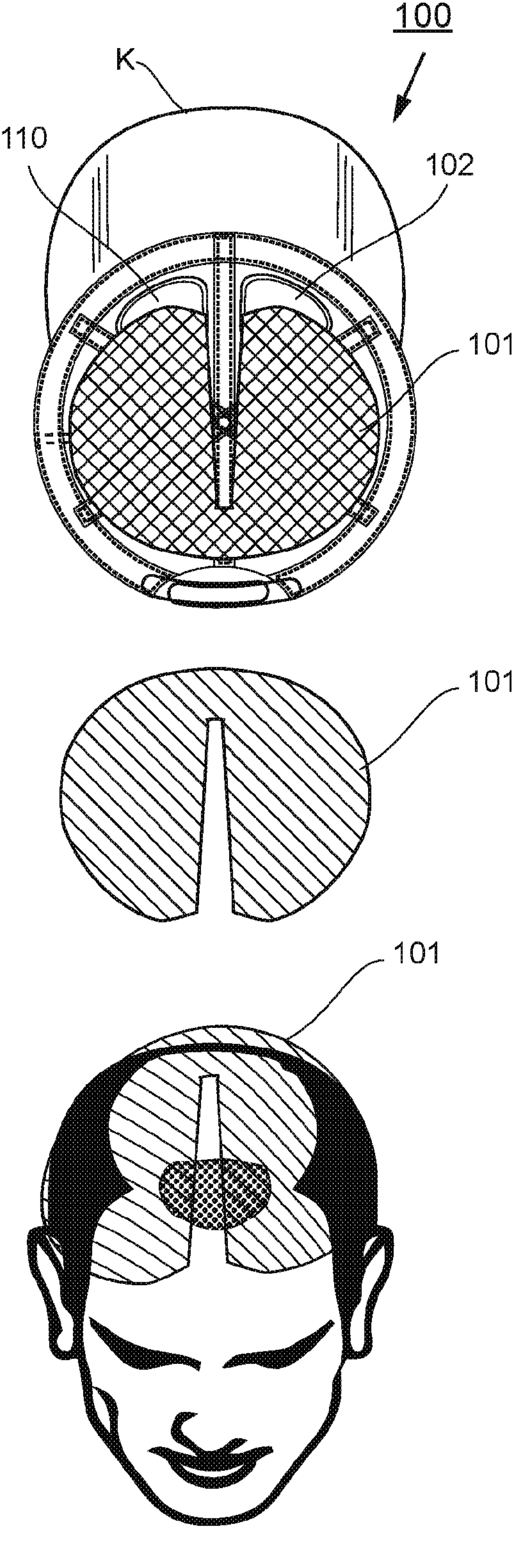
FIG. 11 is a sketch illustrating how an exemplary stimulation electrode lies in a hat liner and comes into contact with the surface of the head.

FIG. 1 shows a first exemplary arrangement of a stimulation device 100 for electrical stimulation of the skin of a user such as the scalp, in the form of a hat which is also referred to herein as a cap K, with an electrical power supply cable 111. The electrical power supply cable 111 can be connected to an electrical power supply such as a battery that is worn on the user's body, for example in an inner jacket pocket. In this exemplary arrangement, the electrical power supply device consists of a rechargeable electrical battery available on the market, such as those available as "power-banks" for cell phones. This exemplary device is suitable to cover long-term stimulation programs with relatively high power consumption.

FIG. 2, on the other hand, shows a second exemplary arrangement 200 of a stimulation device for electrical stimulation of the scalp in the form of a cap K with accumulator 110 which may comprise a battery and a device 105 for wireless data transmission which is alternatively referred to herein as a wireless transceiver. In operative connection with the device 105 for wireless data transmission is a control device 102 which is alternatively referred to herein as control circuitry. The exemplary control circuitry can carry out various programs or stimulation patterns for stimulating the scalp. The control device 102 is in operative connection with at least one detector device 103 which is alternatively referred to herein as a detector. The detector is operative to sense at least one condition that corresponds to an amount of hair on the user's skin adjacent to the detector. The at least one sensed condition corresponding to the hair loss status is usable to determine and select the programs which are alternatively referred to as stimulation patterns herein. Data corresponding to the at least one sensed condition is caused to be sent from the control device 102 and transmitted in wireless signals by the wireless data transmission device 105. Such data may be sent to a cell phone M for analysis. It is also possible in exemplary arrangements to use the cell phone M to send wireless signals to the cap which control or set functional parameters the control device 102.

FIG. 3 shows a sketch of the exemplary stimulation device from FIG. 1 with a view into the cap chuck which accepts a user's head therein. In this bottom view, an exemplary at least one electrode 101 is visible, which is designed here as a foil electrode and occupies approximately the entire area of the cap chuck. Thereby, there are spikes with a round tip on the at least one foil electrode, which are not shown here, which penetrate still existing hair, and rest on a portion of the scalp with their round tip. The spikes do not penetrate the scalp, so that a non-invasive electrode with a large number of contact points is present in engaged relation with a respective portion of the user's skin.

In FIG. 4, the stimulation device of FIG. 2 is shown as a sketch with a view into the cap lining. In this bottom view, at least one electrode 101 is also visible, which is also designed here as a foil electrode with spikes with round tips as a contact point for transmitting the electrical stimuli to the scalp and occupies approximately the entire area of the cap lining. In this exemplary arrangement, the accumulator 110 which may comprise a battery and the integrated control device 102 are also visible approximately in the front area of the cap.

The exemplary at least one stimulation electrode 101 of the stimulation device in FIG. 1 is shown singly in FIG. 5. It can be clearly seen that the at least one foil electrode with spikes with round tips in this arrangement has a concave shape in order to adapt to the approximately ellipsoidal shape of the user's head. Due to the concave shape, the distance between the electrode 101 configured as a foil electrode and the local surface portion of the head with which a respective electrode is engaged is always approximately the same. In this exemplary arrangement of the hair growth stimulation device, the electrode 101 is directly connected to an electric power supply cable 111. However, in FIG. 6, the counterpart is shown without an external power supply cable. This electrode is connected to the accumulator 110 and the control device 102 in FIG. 2.

An alternative to the foil electrodes 101 with spikes and round tips shown in FIGS. 5 and 6 is shown in FIGS. 7 and 8. These exemplary electrodes 101 are designed as individual pins and extend through the scalp hair directly to the scalp, thus creating direct contact with the skin at the scalp surface. These pins also do not penetrate the scalp and form at least one non-invasive scalp electrode. The resulting reduced contact resistance makes it possible to use stimulation pulses with a lower electrical voltage. In FIG. 7, the individual electrodes 101 designed as pin electrodes are connected to the power supply cable 111. In the right-hand illustration in FIG. 8, the same electrodes 101 are shown which are not connected to a power supply cable 111, but these electrodes 101 are operatively connected to the accumulator 110 and the control device 102 in FIG. 2.

FIG. 9 shows a third arrangement of the at least one stimulation electrode 101 in the form of a different electrode arrangement. The electrodes 101 are arranged in a mountain and valley shape. On the slopes of the electrodes 101 are detector devices 103 which are usable to determine the density of the hair H located between them by means of at least one sensed condition which in the exemplary arrangement comprises impedance measurements. The electrical stimulation provided by electrodes 101 is varied by the control device 102 as a function of the at least one measured sensed condition which corresponds to the hair density which is an amount of hair in an area of the skin surface sensed by a detector and in which area an electrode is in engagement. The arrangement of the electrodes 101 can be designed as at least one circumferential electrode, as shown in FIG. 9. However, it is also possible to mount the detector devices 103 on the sides of the pins of the respective electrodes 101 shown in FIGS. 5 and 6.

FIG. 10 shows a matrix of typical hair loss stages. Depending on the physical constitution of the affected person, hair loss progresses through the stages from left to right. Starting on the left with a full head of hair (shaded), a person affected by hair loss goes through a constantly increasing forehead (1st row), or experiences a circular hair loss (2nd row), where the circle always increases in size. At the same time, the progressive stage of hair loss in some differs in that a circular tuft remains in the area of the upper forehead (3rd row). Another variant of hair loss stages is shown in the 4th row. In these stages, the so-called "secret corners" grow until baldness develops here as well, which in all progressions grows into a kind of tonsure. To detect with the detectors these different hair loss stages and to perform the electrical stimulation through the electrodes only in the affected scalp areas, is achieved by the exemplary hair growth stimulation device.

Figure 12:
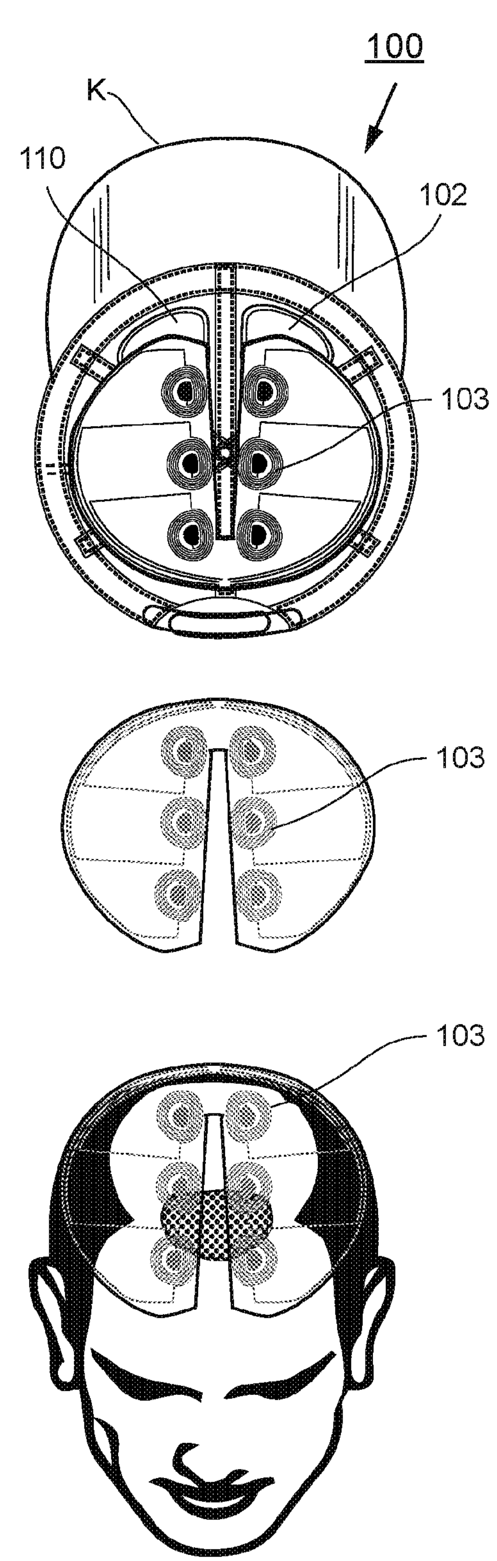
FIG. 12 is a sketch illustrating how an exemplary detector lies in the hat chuck and comes into contact with the surface of the head.

FIGS. 11 and 12 show how the exemplary at least one electrode 101 (FIG. 11) and the exemplary detector device 103 lie directly on top of each other in layers. From above, the individual sketches in FIG. 11 show the view into the lining of the cap with visible foil electrode with spikes with round tips as contact points (cf. FIG. 4). The cap tilts forward out of the paper plane in the middle image with the sun visor. To show the foil electrode in this position, the cap has been hidden in the middle image so that the at least one foil electrode can be seen from the side lying on the lining of the cap K. In this position, the concave foil electrode (cf. FIG. 5 and FIG. 6) or the concave arrangement of individual electrodes (cf. FIG. 7 and FIG. 8) rests on the affected surface portion of the head. In FIG. 12, the detector arrangement 103 is shown directly connected to the foil electrode or to the array of individual electrodes. The exemplary detector device 103 has a plurality of flat coils that can be used to detect the status or degree of hair loss or degree of hair presence at typical locations on portions of the skin of the head via local impedance measurement. In this exemplary arrangement, the detectors are located to the left and right of the fontanel. However, it is also possible to distribute the detectors and electrodes differently in order to be able to detect and treat the typical stages of hair loss.

Figure 13:
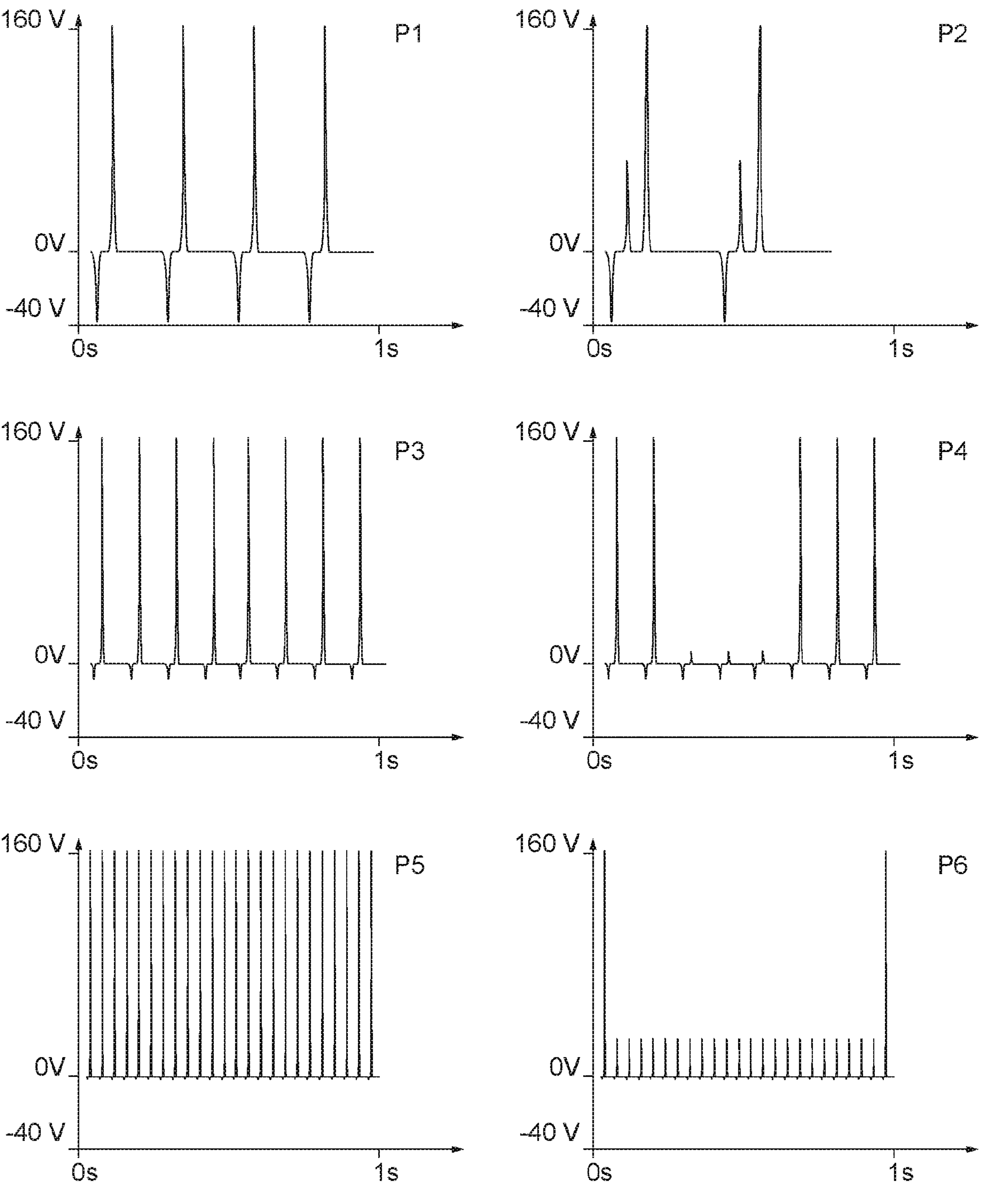
FIG. 13 shows a compilation of exemplary electrical stimulation patterns.

FIG. 13 shows graphically different exemplary electrical stimulation patterns as exemplary programs or patterns P1, P2, P3, P4, P5 and P6 shown which correspond to stored data in connection with the control circuitry. It is possible, for example, to stimulate areas of the scalp with short pulses during which voltage is applied and removed at a frequency of 1 Hz to 4 Hz. In order to increase the effect of the stimulation, it can be provided to first perform a depolarization in the form of applying a reverse or negative voltage, as in the exemplary programs P1 and P2. The depolarization is followed by a polarization with a single pulse as in program P1 or a double pulse sequence having a frequency as in program P2. Exemplary program P3 consists of a somewhat faster pulse sequence with a higher frequency and with uniform pulses without a prior depolarization. It is also possible that the pulses happen in pulse groups, as in exemplary program P4. In exemplary program P5, a pulse sequence of about 25 Hz is shown. Still another pulse sequence is shown in program P6 with low voltage pulses, in which pulses with higher voltage are inserted with a frequency of about 1 Hz. Overall, the frequency of the pulses can be between 1 Hz and 100 Hz, showing different depolarization/polarization patterns, which patterns are determined by the control circuitry responsive at least in part to the at least one sensed condition by the detector in engagement with the portion of the user's skin and caused by the circuitry to electrically stimulate an area of the skin including the portion, in accordance with the pattern through at least one electrode. Of course it should be understood that the structures and electrical stimulation patterns shown are exemplary and in other arrangements other patterns, electrode configurations and detectors may be used.

Figure 14:
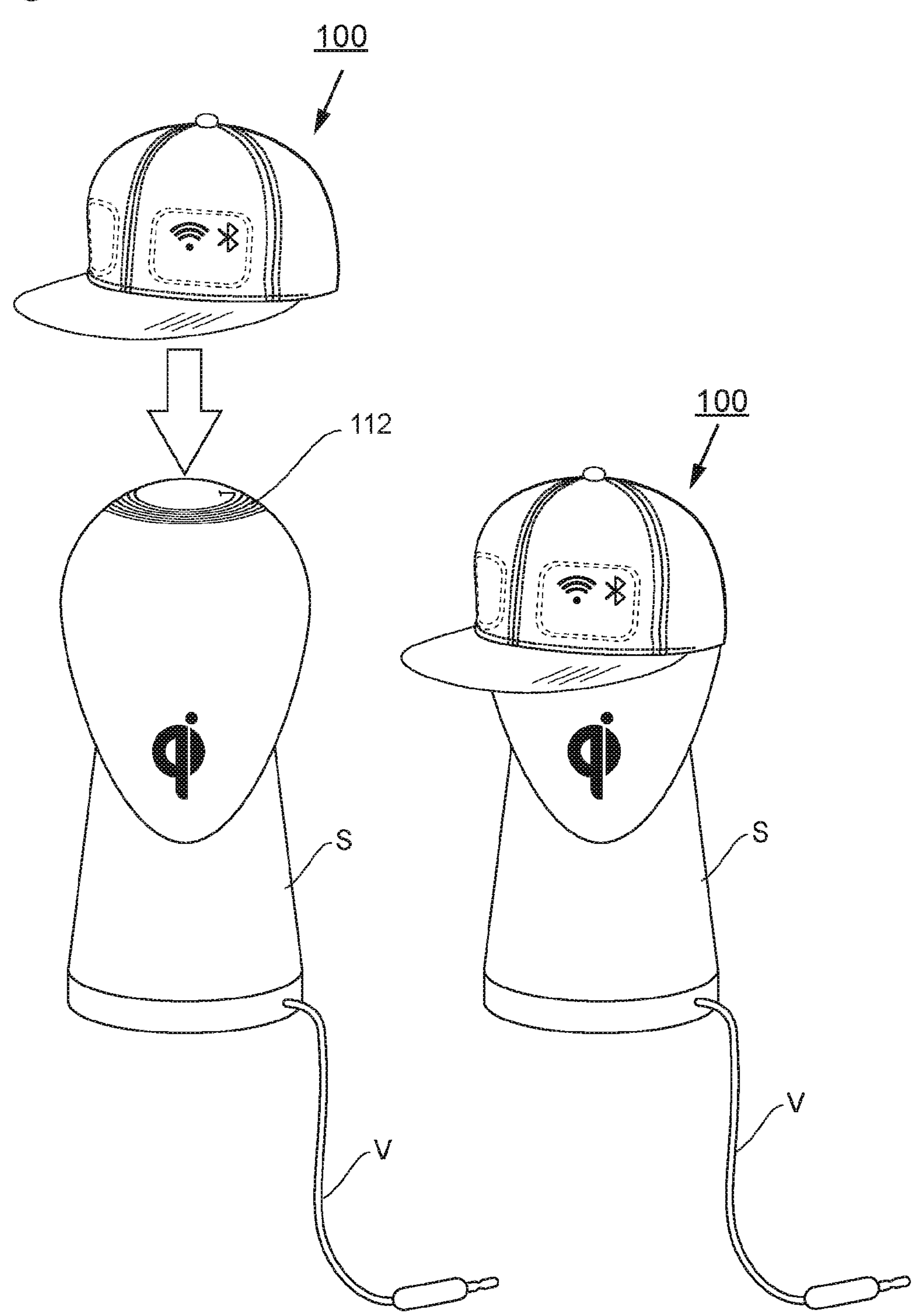
FIG. 14 is a sketch illustrating the storage of an exemplary device on a stand with a contactless inductive charging device.

Finally, FIG. 14 illustrates a stand for the exemplary cap including the scalp hair stimulation device 100 that is reminiscent of a wig stand upon which the device can be removably positioned. A coil 112 is inserted into the upper surface of the stand S, and is connected to a power supply cable V. Via this coil 112, the accumulator 110 of the scalp hair stimulation device can be charged wirelessly via induction through the coil of the device. For this purpose, the Qi protocol, which is also used for cell phones, can be used as the charging protocol. Of course it should be understood that other types of charging connections and approaches may be used.

The exemplary arrangements described herein are suitable for selective non-invasive electrostimulation of areas of hair loss to promote the hair growth in those areas of the head, if it is an arrangement that includes a structure in the form of a hat or cap. Other exemplary arrangements are also suitable for non-invasive electrostimulation of the hair growth of other parts of the body, such as, for example, the hair on the chest or the back, the hair on the armpits, the hair on the pubic region or for stimulating beard growth, if it is an arrangement in the form of another article of clothing. For this purpose, exemplary arrangements may comprise a device designed as a wearable device in the form of a garment as a so-called "wearable", for example in the form of an outer garment, such as an undershirt, a T-shirt, a shirt, a sweater, a jacket, underpants, sports underpants, an elastic bandage, such as a bandage for supporting the back muscles, or as a scarf or a beard bandage. Of course these arrangements are exemplary and in other arrangements other approaches and arrangements may be used.

Thus the exemplary arrangements achieve improved operation, eliminate difficulties encountered in the use of prior devices, and attain the useful results that are described herein.

In the foregoing description certain terms have been used for brevity, clarity and understanding. However, no unnecessary limitations are to be implied therefrom because such terms are used for descriptive purposes and are intended to be broadly construed. Moreover the descriptions and illustrations herein are by way of examples and the new and useful features are not limited only to those features that have been shown and described.

Further it should be understood that the features and/or relationships associated with one exemplary arrangement can be combined with features and/or relationships of another arrangement. That is, various features and/or relationships from various arrangements can be combined into further arrangements. The new and useful scope of the disclosure is not limited only to the arrangements that have been shown and described.

Having described features, discoveries and principles of the exemplary arrangements, the manner in which they are constructed and operated, and the advantages and useful results attained, the new and useful features, devices, elements, arrangements, parts, combinations, systems, equipment, operations, methods, processes and relationships are set forth in the appended claims.

REFERENCE LIST

| | | | |
|---|---|---|---|
| 100 | Stimulation device | K | Cap |
| 101 | Electrode | M | Cell phone |
| 102 | Control device | P1 | Program |
| 103 | Detector device | P2 | Program |
| 104 | Humidity sensor | P3 | Program |
| 105 | Device for wireless data transmission | P4 | Program |
| | | P5 | Program |
| 110 | Accumulator | P6 | Program |
| 111 | Power supply cable | S | Stand |
| 112 | Coil | V | Electrical supply cable |
| 200 | Stimulation device | | |

The invention claimed is:

1. Apparatus configured to stimulate hair growth comprising:

an electrode, wherein the electrode is configured to electrically stimulate a portion of a user's skin surface that is in contact with the electrode, includes a plurality of projections, wherein the plurality of projections are configured to protrude through hair of the user and rest in engagement with the portion of the skin surface without skin penetration, a detector, wherein the detector is operative to sense at least one condition that directly corresponds to an amount of hair that is present on the user's skin surface in an area that includes the portion of the skin surface, control circuitry, wherein the control circuitry is in operative connection with the electrode and the detector, wherein responsive at least in part to the at least one sensed condition the control circuitry is operative to determine an electrical stimulation pattern, and cause the electrode to electrically stimulate the area in accordance with the determined electrical stimulation pattern.

2. The apparatus according to claim 1 wherein the control circuitry includes stored data corresponding to a plurality of different stimulation patterns, wherein in making the determination the control circuitry selects data corresponding to one of the stimulation patterns.

3. The apparatus according to claim 1 wherein the electrode projections include at least one of spikes with round tips, pins, and mountain and valley shapes.

4. The apparatus according to claim 1 wherein the apparatus includes a plurality of disposed electrodes, and a plurality of disposed detectors, wherein each electrode is in contact with a different respective portion of a user's skin than the other electrodes, wherein each detector is operative to sense the at least one condition in a respective area of the user's skin that is different from the areas of the user's skin in which the at least one condition is sensed by the other detectors, wherein each respective area of the user's skin in which the at least one condition is detected by a respective detector includes a respective portion of the user's skin which is in contact with a respective electrode, wherein the control circuitry is operative responsive at least in part to the at least one condition detected in a first respective area of a user's skin to determine a first electrical stimulation pattern, and cause the electrode in contact with the user's skin in the first respective area to electrically stimulate the first respective area in accordance with the determined first electrical stimulation pattern, and responsive at least in part to the at least one condition detected in a second respective area of the user's skin that is disposed away from the first respective area, to determine a second electrical stimulation pattern that is different from the first electrical stimulation pattern, and cause the electrode in contact with the user's skin in the second respective area to electrically stimulate the second respective area in accordance with the determined second electrical stimulation pattern.

5. The apparatus according to claim 1 and further comprising:

a humidity sensor, wherein the humidity sensor is operative to sense at least one property from which electrical conductivity of the user's skin in the area can be determined, wherein the humidity sensor is in operative connection with the control circuitry, wherein the control circuitry is operative to determine the electrical stimulation pattern responsive at least in part to the at least one property sensed by the humidity sensor.

6. The apparatus according to claim 1 wherein the electrical stimulation pattern corresponds to pulses each including application and removal of a voltage to the electrode at a frequency.

7. The apparatus according to claim 1 wherein the electrical stimulation pattern corresponds to pulses including application and removal of at least one positive voltage and at least one negative voltage to the electrode.

8. The apparatus according to claim 1 wherein the electrical stimulation pattern corresponds to pulses including application and removal of different voltages to the electrode at different respective frequencies.

9. The apparatus according to claim 1 wherein voltage magnitude and frequency of the determined electrical stimulation pattern varies responsive at least in part to the at least one sensed condition.

10. The apparatus according to claim 1 and further comprising:

a wireless transceiver, wherein the wireless transceiver is in operative connection with the control circuitry, wherein the control circuitry is operative to cause at least one of the wireless transceiver to transmit signals indicative of a status of the apparatus, and the apparatus to operate in accordance with at least one operational characteristic responsive to signals received by the wireless transceiver.

11. The apparatus according to claim 1 and further comprising:

a wireless transceiver, wherein the wireless transceiver is in operative connection with control circuitry, wherein the control circuitry is operative to cause the electrical stimulation provided by the electrode to change responsive at least in part to wireless signals received through the wireless transceiver.

12. The apparatus according to claim 1 and further comprising:

a hat, wherein the hat is configured to be removably positioned on a head of the user, wherein the electrode and the detector are in operatively supported connection with the hat.

13. The apparatus according to claim 1 and further comprising:

a battery, wherein the battery is in operative connection with the control circuitry, a coil, wherein the coil is in operative connection with the battery, wherein the coil is configured to charge the battery via induction, a hat, wherein hat is configured to be removably positioned on a head of the user, wherein the electrode, detector, coil, battery and control circuitry are in operative supported connection with the hat.

14. The apparatus according to claim 1 and further comprising:

a battery, wherein the battery is in operative connection with the control circuitry, a coil, wherein the coil is in operative connection with the battery, wherein the coil is configured to charge the battery via induction, a hat, wherein hat is configured to be removably positioned on a head of the user, wherein the electrode, detector, coil, battery and control circuitry are in operative supported connection with the hat, a stand, wherein the stand is configured to removably support the hat in operatively engaged relation therewith, wherein the stand includes a stand coil, wherein the stand coil is configured to inductively charge the battery via the coil.

15. Apparatus configured to stimulate hair growth comprising:

a plurality of electrodes, wherein each electrode is disposed from each other electrode, includes at least one projection, wherein each projection is configured to protrude through hair of a user and rest in engagement with user skin without skin penetration, a plurality of detectors, wherein each detector is disposed from each other detector, is operative to sense at least one condition that directly corresponds to an amount of hair that is present on the user's skin in a respective skin area corresponding to the respective detector, wherein the respective skin area is electrically stimulatable through operation of a respective electrode, control circuitry, wherein the control circuitry is in operative connection with each of the plurality of electrodes and each of the plurality of detectors, wherein responsive at least in part to the at least one sensed condition sensed by each respective detector in each respective skin area, the control circuitry is operative to cause determination of an electrical stimulation pattern, and electrical stimulation by each respective electrode of each respective skin area in accordance with the determined electrical stimulation pattern.

16. The apparatus according to claim 15 wherein responsive at least in part to the at least one sensed condition sensed by another respective detector in another respective skin area, the control circuitry is operative to cause determination of another electrical stimulation pattern, and electrical stimulation by another respective electrode of the respective another skin area in accordance with the determined another electrical stimulation pattern.

17. The apparatus according to claim 15 wherein voltage magnitude and frequency of the determined electrical stimulation pattern varies responsive at least in part to the at least one sensed condition.

18. The apparatus according to claim 15, and further comprising:

a moisture sensor, wherein the moisture sensor is operative to sense at least one property from which electrical conductivity of the user's skin surface in the skin area can be determined, wherein the moisture sensor is in operative connection with the control circuitry, wherein the control circuitry is operative to determine at least one stimulation parameter of the electrical stimulation pattern responsive at least in part to the at least one property sensed by the moisture sensor.

19. The apparatus according to claim 15, and further comprising:

a wireless transceiver, wherein the wireless transceiver is operative to receive wireless signals, and is in operative connection with the control circuitry, wherein the control circuitry is operative to change the electrical stimulation by the respective electrode responsive at least in part to the received wireless signals.

20. The apparatus according to claim 15 and further comprising:

a hat, wherein the hat is configured to be removably positioned on a head of the user, wherein the plurality of electrodes, the plurality of detectors and the control circuitry are in operative supported connection with the hat.

21. The apparatus according to claim 15 and further comprising:

a battery, wherein the battery is in operative connection with the control circuitry, a hat, wherein the plurality of electrodes, the plurality of detectors, the battery and the control circuitry are in operative supported connection with the hat, wherein the hat is configured to be removably positioned on each of a head of the user and a stand configured to charge the battery.

22. Apparatus configured to stimulate hair growth comprising:

an array including a plurality of electrodes, wherein each electrode is disposed from each other electrode, includes at least one projection, wherein each projection is configured to protrude through hair of a user and rest in engagement with user skin without skin penetration, a plurality of detectors, wherein each detector is disposed from each other detector, is operative to sense at least one condition that directly corresponds to an amount of hair that is present on the user's skin in a respective skin area adjacent to the respective detector, wherein the respective skin area is electrically stimulatable through operation of a respective electrode, control circuitry, wherein the control circuitry is in operative connection with each electrode and each detector, wherein responsive at least in part to the at least one sensed condition sensed by each respective detector, the control circuitry is operative to cause determination of an electrical stimulation pattern, and electrical stimulation by at least some of the respective electrodes of the respective skin areas in accordance with the determined electrical stimulation pattern.

23. The apparatus according to claim 22, and further comprising:

a wireless transceiver, wherein the wireless transceiver is operative to receive wireless signals, and is in operative connection with the control circuitry, wherein the control circuitry is operative to change the electrical stimulation by the electrodes responsive at least in part to the received wireless signals.

24. The apparatus according to claim 22 and further comprising:

a hat, wherein the electrodes, the detectors and the control circuitry are in operative supported connection with the hat, wherein the hat is configured to be removably positioned on each of a head of the user and a stand configured to charge the battery.

* * * * *